United States Patent [19]

Deming et al.

[11] 4,399,349
[45] Aug. 16, 1983

[54] ELECTRICALLY HEATED FACIAL SAUNA APPLIANCE

[75] Inventors: Loretta M. Deming, Stamford; Raymond W. Kunz, Monroe, both of Conn.

[73] Assignee: Clairol Inc., New York, N.Y.

[21] Appl. No.: 249,052

[22] Filed: Mar. 30, 1981

[51] Int. Cl.³ .............. A61H 33/12; F22B 1/28; H05B 3/00

[52] U.S. Cl. .................. 219/276; 4/535; 4/537; 68/222; 128/203.17; 128/368; 219/273; 219/362; 261/142

[58] Field of Search .............. 219/271–276, 219/362, 222, 242; 128/203.17, 203.27, 368; 261/141, 142; 4/535–537; 68/222

[56] References Cited

U.S. PATENT DOCUMENTS

| | | |
|---|---|---|
| 2,343,458 | 3/1944 | Hettinger . |
| 2,561,443 | 7/1951 | March .................. 219/271 |
| 3,511,236 | 5/1970 | Conlin et al. . |
| 3,546,428 | 12/1970 | Omohundro et al. ...... 219/271 |
| 3,654,780 | 4/1972 | Frank ................. 219/271 X |
| 3,695,066 | 10/1972 | Doyel ................ 219/271 X |
| 3,742,629 | 7/1973 | Plasko .................. 38/69 |
| 3,745,306 | 7/1973 | Naritomi .............. 219/272 |
| 3,873,806 | 3/1975 | Schossow .............. 219/273 |
| 3,949,743 | 4/1976 | Shanbrom ............ 128/203.17 |
| 4,190,052 | 2/1980 | McCarthy ............. 128/368 |
| 4,300,556 | 11/1981 | Ochi et al. ............ 128/368 |

FOREIGN PATENT DOCUMENTS

| | | |
|---|---|---|
| 383484 | 2/1922 | Fed. Rep. of Germany ......... 128/203.27 |
| 53-9669 | 1/1978 | Japan .................. 4/537 |

Primary Examiner—A. Bartis
Attorney, Agent, or Firm—Isaac Jarkovsky; John J. Balser; Stuart E. Krieger

[57] ABSTRACT

An electrically heated, hand-held portable facial sauna appliance has a top air inlet, side air inlet, an air flow adjustment arrangement and a fan to mix ambient air with steam generated from a quantity of water contained in an internal steam generating chamber having an associated electric heater and a bottom fill opening such that the appliance must be inverted to fill the chamber with water. A water trap and overflow arrangement in the container ensures that the chamber cannot be overfilled and enables the appliance to be overturned during use without leaking. The appliance is provided with attachments in the form of a facial mask, concentrator tube, brush and sponge, each designed to fit over a steam-air mixture outlet and control the quantity of air entering through the top air inlet.

20 Claims, 8 Drawing Figures

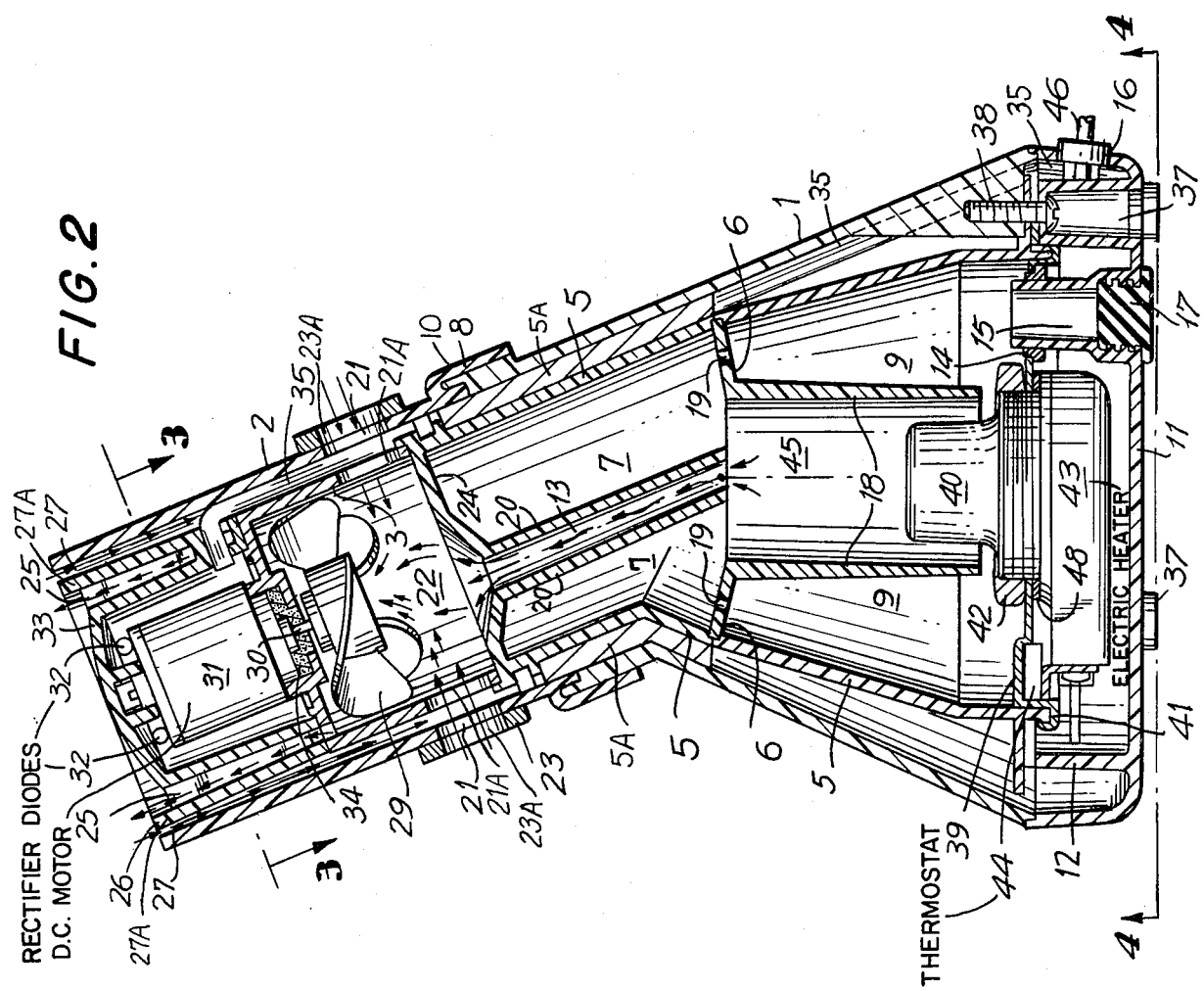

ELECTRICALLY HEATED FACIAL SAUNA APPLIANCE

BACKGROUND

1. Field of the Invention

This invention relates to hand-held electrically powered steam generating devices, such as a facial sauna, which cannot be overfilled, can be tilted in any direction when full without leaking and can mix air and steam in any desired proportions to control the concentration and temperature of the emitted steam. In addition, the facial sauna can be adapted to receive attachments such as a facial mask, concentrator, brush or sponge.

2. Prior Art

Prior steam generating devices and facial saunas have structures which permit them to be tilted in any direction without spilling. However, for the most part, these prior steam generating devices and facial saunas must be filled with a measured amount of liquid. In addition, they are not made to receive a self limiting amount through a fill means in the base.

Thus, Hettinger, U.S. Pat. No. 2,343,458, issued Mar. 7, 1944 discloses a vaporizer constructed of two cylinders or cups of sheet metal which are telescoped so that they form, respectively, the bottom and inside of the container and outside and top of the container. The top is provided with an aperture at one side for reception of a long spout which extends within the container for a substantial distance and is inclined at a sufficient angle to the vertical to prevent the user from getting burned if the device is tipped forward. The long inclined extension prevents water from running out of the spout if the container is not filled above a line marked on it.

Omohundro, U.S. Pat. No. 3,546,428, issued Dec. 8, 1970 discloses a steam generator which includes a water tank, electric heating unit and a spout that both expels steam from the water tank and receives water for introduction into the water tank. The spout has an inner portion extending into the water tank and spaced from the walls of the water tank a distance sufficient to permit retention of a predetermined amount of water, i.e., 28–35 cubic centimeters, within the tank after filling while the steam generator is in an upright position and then inverting to pour out excess water. There is no structure which permits filling the water tank from the bottom. Also, Omohundro provides an extension having holes, which extension connects on the end of the spout to increase the velocity of the steam as it is being expelled and permits the expelled steam to mix with ambient air, lowering the temperature of the steam. No fans or adjustable air intakes are used.

Doyel, U.S. Pat. No. 3,695,066, issued Oct. 3, 1972 discloses a portable hand-held steamer in which the housing is shaped so that when a certain quantity of water is contained therein, the housing has a capacity to contain the quantity of water in all directions taken about the geometric center thereof. A water fill hole is provided in the upper housing. A water measuring cup is provided which is designed to hold no more than the amount of water that is desirable to use in the vapor generator.

Plasko, U.S. Pat. No. 3,742,629, issued July 3, 1973 discloses a portable hand-held electric clothes steamer with a one piece housing having an integral fill opening intermediate a water chamber and a combined steam chamber and water trap. The fill opening is positioned so that the water will overflow the opening when the proper amount is in the chamber. This enables the water trap to work effectively and prevents the water from leaking out when the device is overturned.

Conlin, et al., U.S. Pat. No. 3,511,236, issued May 12, 1970 discloses a vaporizer in which air is drawn in by a fan through adjustable openings in the housing and is delivered to the vaporizing chamber. The steam generator of the present invention includes a fan which mixes air with the steam after the steam leaves the vaporizing chamber.

Naritomi, U.S. Pat. No. 3,745,306, issued July 10, 1973 discloses a steam generating instrument for hair dressing having a blower and steam generating means wherein the blower delivers the steam from the steam generating means into a venting duct and then to the hair.

There are no steam generating devices such as facial saunas which are filled from the bottom and cannot be overfilled, can be tilted in any direction without spilling or leaking and have the temperature of the steam controlled by mixing with air in the steam outlet pathway utilizing a fan and adjustable air inlet holes in the housing between the fan and steam generator.

BRIEF SUMMARY OF THE INVENTION

This invention provides a portable, hand-held, leak-proof, electric steam generating apparatus which in its preferred embodiment is a facial sauna.

The apparatus comprises a generally circular housing with a lower portion having a larger circumference than the upper portion which generally acts as a steam outlet nozzle. The lower housing has in its base a water fill tube leading to a water tank inside the base. The base of the water tank seals the lower portion of the lower housing from the water or other aqueous fluid in the water tank. There are interior baffle portions in the lower housing which define the lower portion of the water tank. A heater having a heating element is in the sealed off portion of the lower housing and has a heat transfer surface in the water tank to generate steam.

The upper housing which is sealed to the lower housing by a lap seam has air inlet means with means to control the volume of air, e.g. a circumferential row of air inlets between the top of the upper housing and the lap seam with a rotatable ring having holes around the upper outer housing over the circumferential row of air inlets. The ring is rotated to control the air flow volume. The housing contains walls defining an upper portion of the water tank connected to the lower portion of the water tank by passageways in a common baffle. The upper water tank inner baffle defines a steam exit pathway from the portion of the water tank where the steam is generated. The upper water tank also acts as a water trap when the apparatus is overturned. The steam exit pathway connects said steam generating area to a steam-air mixing chamber in a portion of the upper housing where the air enters from, e.g. the circumferential row of air inlets and preferably a second annular air inlet. A fan and a motor are attached to a motor housing defined by walls in the center top portion of the upper housing, with the fan in the steam-air mixing chamber. The steam mixed with air by the fan exits through an annular steam outlet around the motor housing. The second air inlet system which is a preferred construction is an annular air inlet between the annular steam outlet and the outer wall of the upper housing and is separated from the annular steam outlet by an inner wall in the upper housing. The inner wall has openings so the air can reach the air-steam mixing chamber. Another means to regulate the temperature is by use of specially structured attachments, i.e., brush, sponge, concentrator and facial mask.

BRIEF DESCRIPTION OF THE DRAWINGS

FIG. 2 is a side elevational section of the preferred embodiment of this invention;

FIG. 3 is a top view of the air and steam outlets of this invention taken through line 3—3 of FIG. 2;

DETAILED DESCRIPTION OF PREFERRED EMBODIMENT

The preferred embodiment of this invention is an electric, hand-held, portable facial sauna having an outer housing that is shaped generally like a round flask with a slanted elongated neck. Inside the housing are a base defining an electrical enclosure, a lower housing enclosing a water tank-steam generating chamber, the upper part of the water tank functions as a water trap and has a steam exit passageway. The upper housing contains air inlets, a motor and fan in an air-steam mixing chamber and steam outlets. The water tank can never be overfilled; it is filled with the required amount of liquid e.g., water or aqueous solutions or emulsions containing medicaments, colognes or perfumes, moisturizers and the like, without the need to measure or utilize markings on the housing. The tank is filled from the bottom through a fill tube which conducts the liquid into the lower part of the water tank and thence into the upper part of the water tank. When the tank is full, the excess water will begin to run out the top of the sauna through the steam outlet. When this occurs, the sauna is placed upright. Subsequent tilting or overturning will not cause liquid to run out since it is trapped by baffles in the tank around the steam generating area and steam exit pathway. The water tank is constructed so that no matter which way the sauna is tilted, there is sufficient volume in the water tank around the point at which the steam exit passageway begins, to hold all the water. In the most preferred embodiment this point occurs at the intersection of the axial center lines of the upper and lower parts of the water tank.

The upper housing contains air inlets through which air is drawn in by the fan and mixed with the steam from the steam generating area to cool the steam to a desired temperature. The amount of air drawn in by the fan is controlled by a rotating ring as described hereinafter. In addition, attachments such as a facial mask, concentrator tube, brush attachment and sponge attachment are structured so that when they are attached to the steam outlet they restrict air inflow from an air inlet in the top of the upper housing to the minimum amount of air required for safe use.

Figure 4:
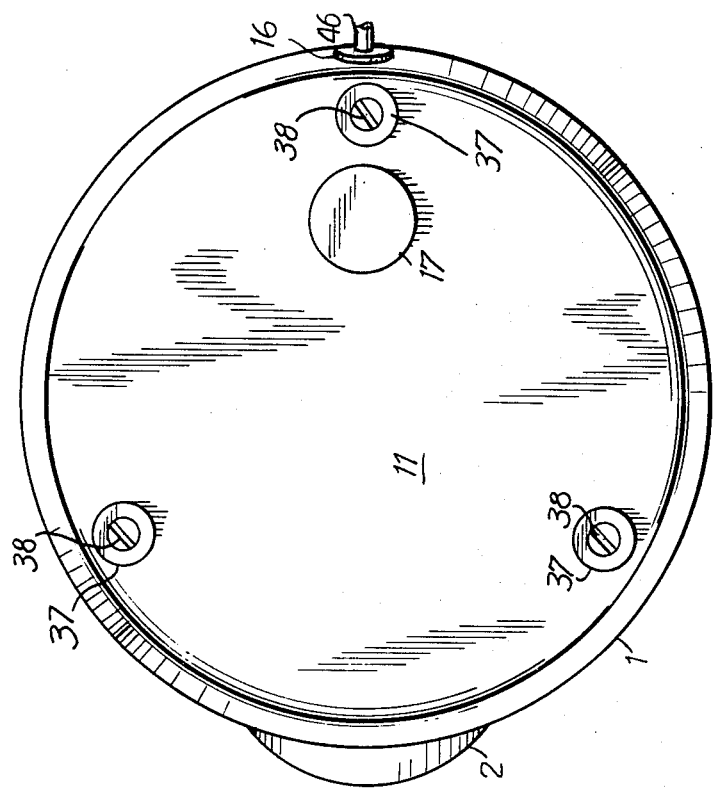
FIG. 4 is a bottom view showing the legs and a fill tube taken through line 4—4 of FIG. 2.
Figure 1:
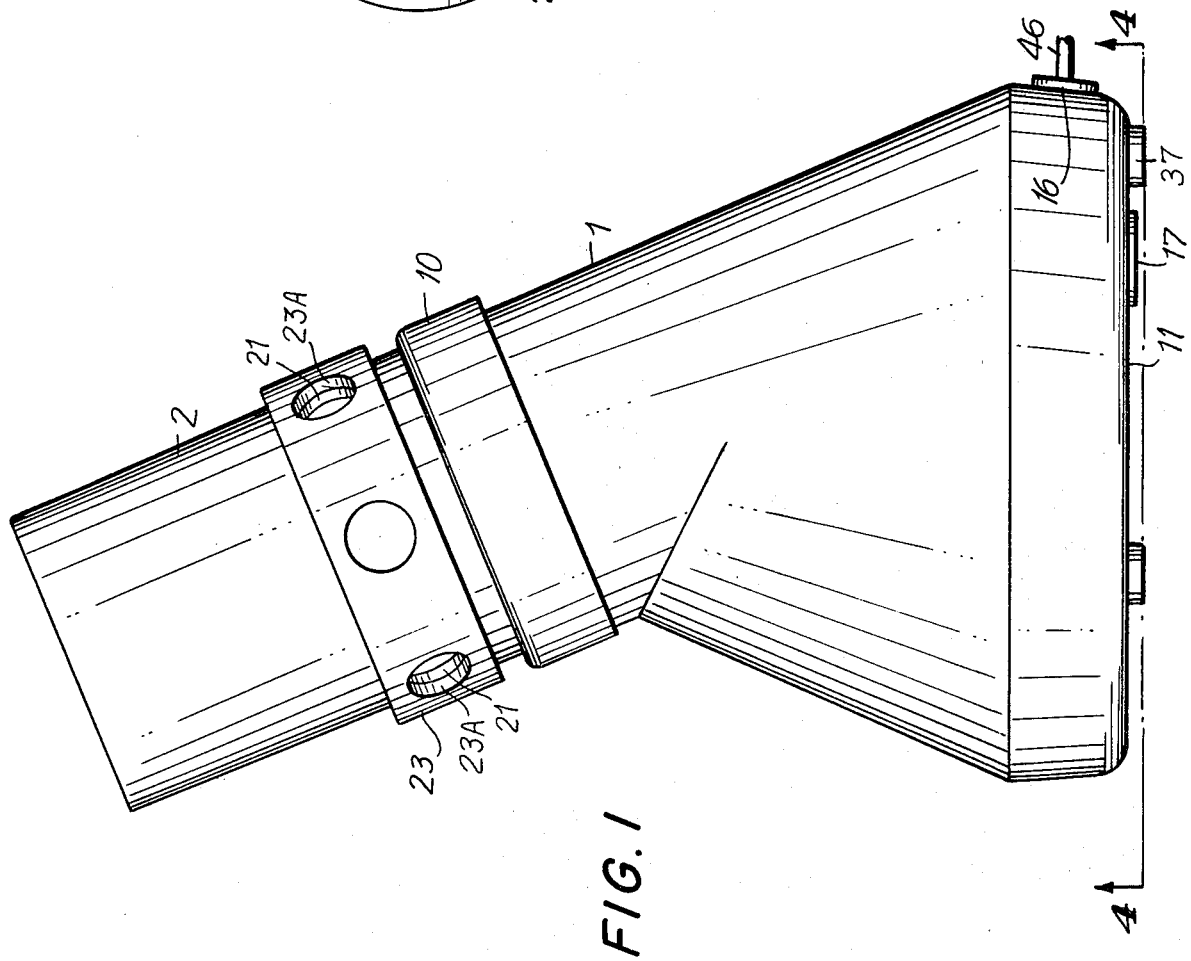
FIG. 1 is a side elevational view of the preferred embodiment of this invention.

With reference to FIGS. 1-4, the outer housing of the facial sauna provided by this invention is comprised of a lower housing 1, and an upper housing 2 made of molded heat and impact resistant plastic such as ABS, an acrylonitrile butadiene styrene plastic. The upper housing 2 and the lower housing 1 are attached by, e.g., a lap seam 8. The seam 8 is sealed by conventional means, e.g., ultrasonic means, and is covered by a decorative ring 10. The base 11 of the lower housing 1 is detachable and is held in place by screws 38 which also hold feet 37 to the base 11. The feet 37 provide a cushion for the sauna to rest on. There are usually three feet 37. The base 11 is made of an impact and heat resistant moldable plastic such as phenolic resin and the feet are made of a resilient plastic.

The base 11 has two openings, one for a water fill tube 15 and one for a power cord 16. The water fill tube 15 is sealed, after the sauna is filled, by a screw plug 17. The tube 15 and plug 17 are made of moldable heat resistant plastic with a coefficient of expansion such that the plug will not loosen when cold and not bind when hot. The fill tube 15 passes through a hole in the base plate 39 of the lower water tank 9 and is sealed against water leakage through the tank base plate 39 by a plastic grommet 14 such as one made from, for example, ethylene-propylene.

The base 11 which is sealed against water by a base inner wall 12 at the sides and a metal bottom plate 39 on the lower tank 9 has a resistance heater 43 therein in which the heating element is enclosed. The heater 43 has a heat transfer dome 40 on the top thereof. The dome 40 projects through a hole in the metal bottom plate 39 into the steam generating chamber 45 which is enclosed by the interior baffles 18 of the lower water tank 9. The heat transfer dome 40 is sealed against leakage through the hole in the tank bottom plate 39 by a gasket 48. The heater 43 is fastened to the plate 39 by a nut 42. The heater housing 43 shown in FIG. 2 is made of diecast aluminum. Other suitable heaters such as a ceramic resistance or positive temperature coefficient (PTC) heater enclosed in an aluminum case can also be used.

A thermostat 44 calibrated to about 100°-110° C. is attached to the heater 43 and the underside of the tank base plate 39.

The base 11 also has a hole 16 for a power cord 46 which powers the heater 43 and the fan motor 31 in the upper housing 2. The wiring for the fan motor 31 is in a wiring tube 35 which extends from inside the base 11 along the inside of the walls of the lower outer housing 1 and upper outer housing 2 through the motor housing 33 to the motor 31. The wiring tube 35 is supported on the inside by the lower inner housing (water tank housing) 5 and upper inner housing 3.

The lower tank 9 and the upper tank 7 are defined by the tank housing 5; the upper tank 17 being separated from the lower housing 1 by a partially angulated annular casing 5A. The lower tank is annular shaped and is defined by the tank housing 5 as the outer wall, inner baffle 18 which surrounds the inner chamber 45, and bottom plate 39 which is water-tightly sealed to the outer wall of the tank housing 5 by conventional sealing means, for example, a crimp 41 as illustrated in FIG. 2. The top baffle 6 of the lower tank 9 separates the lower tank 9 from the upper tank 7. However, in order for water to pass between the upper tank 7 and the lower tank 9, there are holes 19 in the top baffle 6 of the lower tank 9 which is also the floor of the upper tank 7.

The upper tank 7 is annular and its outside wall is the tank housing 5, its inside baffle 20 forms a steam exit passageway 13 for the steam generated from the inner chamber 45 to travel to the air-steam mixing chamber 22, as shown by the wavy arrows. The top 24 of the upper tank 7 seals it from the air-steam mixing chamber 22. When the water tanks 7 and 9 are in the process of being filled through the fill tube 15, they reach a point at which they are full. When more water is added through the fill tube 15, it overflows into the steam exit pathway 13 and thence out the steam outlet 25. This prevents excess water from entering into and staying in the system. When the sauna is turned upright then overturned, the water in the tanks 7 and 9 is trapped by the baffles 18, 19, 20 and 24 and the wall 5. Other water traps such as valves can be used but are not preferred.

The water tanks 7 and 9 hold a sufficient volume of water to enable the sauna to operate for about 10 to 12 minutes before refilling is necessary. The tank capacity is about 65 to 75 cubic centimeters. Of course, these dimensions can be changed to suit any particular design or use of a steam generating device which may not necessarily be a facial sauna.

In the upper part of the upper outer housing 2 is contained a motor housing 33 having therein a DC fan motor 31 connected to the writing leading to the power cord 46 and having diodes 32 as a bridge rectifier. In addition, the motor 31 rests on a foam gasket 34 which is on the bottom of the motor housing 33. The foam gasket 34 helps reduce vibration. On a shaft 30 extending through the bottom of the motor housing 33 from the motor 31 is an axial fan 29. Although an axial fan is illustrated, other fans such as centrifugal or transverse types can be used. The fan 29 draws air from air inlet holes 21 in the upper housing 2 placed circumferentially near the bottom of air-steam mixing chamber 22 and an annular air inlet 27 as hereinafter discussed. The air inlet holes 21 are aligned with similar sized holes 21A in wall 3. The air inlet holes 21 are covered by a rotating sliding ring 23 which has holes 23A in it about the same size and number as the air inlet holes 21. The ring 23 is slidably supported on the upper outer housing 2. When the ring 23 is rotated the inlet holes 21 are either covered, partially covered or uncovered, thus controlling the amount of air flow. Generally, the amount of air led in should be sufficient to cool the steam enough so it will not scald the operator. The wall of the motor housing 33 forms an inside wall of an annular steam outlet 25. The steam-air mixture from the mixing chamber 22 is blown through the steam outlet 25 by the fan 29. The bottom of the outlet 25 passes the base of the motor housing 33 through large apertures between radial bars 50 which fix the housing 33 to the outer wall 3 of the steam outlet 25. The outer wall 3 of the steam outlet 25 is attached by radial bars 26 at the top to the upper outer housing 2 and at the bottom to the top of the upper tank 7. There are holes 21A in the inner wall 3 which match the air inlet holes 21 in the upper housing 2, enabling air to enter the mixing chamber 22. An annular air inlet 27 is defined by the upper outer housing 2 and an upper inner wall 3. The air enters, as shown by the straight arrows, through the spaces 27A between the bars 26, flows down the air inlet passage 27 and enters the mixing chamber 22 through the circumferential row of holes 21A in the inner wall 3 where it mixes with the steam generated in the inner chamber 45, as shown by the presence of straight and wavy arrows.

Figure 7:
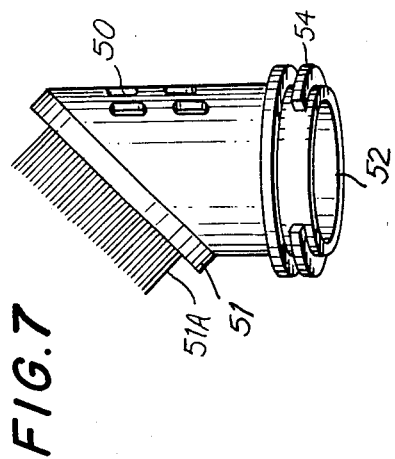
FIG. 7 is a perspective view of a brush attachment.
Figure 8:
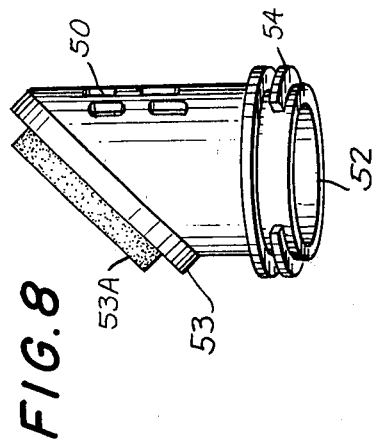
FIG. 8 is a perspective view of a sponge attachment.
Figure 5:
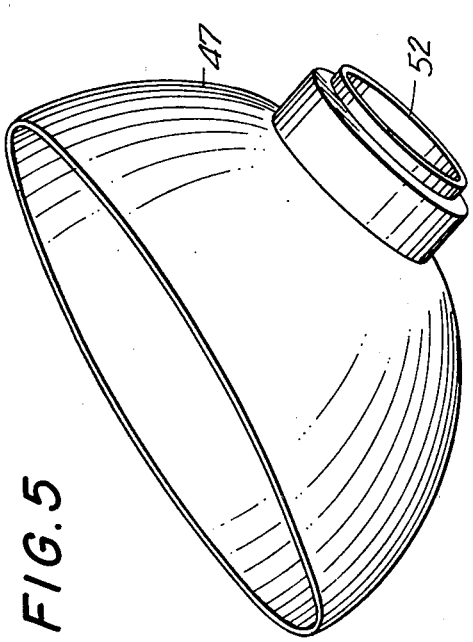
FIG. 5 is a perspective view of the facial mask attachment.
Figure 6:
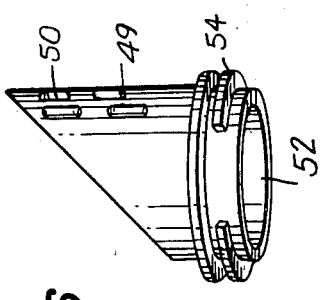
FIG. 6 is a perspective view of a concentrator tube attachment.

The amount of air entering the air inlet 27 is controlled by the attachments shown in FIGS. 5–8 which attach to the outlet end of the facial sauna by e.g., a bayonet attachment. The attachments, i.e., facial mask 47, concentrator tube 49, brush attachment 51 and sponge attachment 53 are hollow to allow the steam-air mixture to escape. Except for the facial mask, they have segmented lower flanges 54 on their attaching ends 52. The attaching end 52 is inserted into the annular steam outlet 25 so as to occupy its outer circumference while permitting the steam-air mixture to escape through the inner circumference of the steam outlet 25 and subsequently through the attachment. The segmented flanges 54 rest on top of the facial sauna while allowing air flow to pass first through the segmented portion and then through air inlet 27 to the extent needed to ensure a safe steam-air mixture temperature at a predetermined level. The size of the segments varies depending on the particular predetermined temperature level desired. These attachments allow the user different proximity to the air-steam mixture because of their different uses and shapes. Thus, the sponge attachment 53 and brush attachment 51 allow the user to place bristles 51A and sponges 53A, respectively, directly on the skin. In order to prevent the user from being scalded, the amount of air entering the mixing chamber has to be controlled. This is done by making the openings in the segmented flanges 54 of a size which will permit sufficient air to enter the top air inlet 27 and by controlling the side air inlets 21 with the rotating ring 23.

In order to prevent the air-stream mixture from becoming too hot if the user blocks the top of the attachment, slots 50 are provided in the walls thereof which permit the air-steam mixture to escape. The facial mask 47 need not have slots because it cannot readily be blocked, however, if desired slots can be provided.

The attaching flanges 52 of the facial mask 47 preferably have no segments and the openings between the segments 54 of the concentrator 49 need not be as wide as those for the brush 51 and sponge 53 because the temperature need not be as cool since the user can move the face away from the steam-air outlet into a cooler region and still obtain the desired effect. However, since it is still possible to block the concentrator 49, slots 50 are provided in the walls thereof.

An alternative construction could eliminate the top air inlets 27, however, in this case, stops on the rotatable ring 23 would be needed to insure that at all times air is being brought in to mix with the steam. Another alternative construction could provide detachable heads on the attaching ends 52.

The upper outer housing 2 is angled from the vertical for ease of use and manufacture. The upper housing 2 need not be angled, however, the sauna operates satisfactorily when the upper housing 2 is angled from about 0° to 90° from the vertical. The preferred angle is generally about 23°.

In use the sauna operates as follows, the operator takes the empty, cold sauna and turns it upside down, then removes the plug 17 from the water fill tube 15 and pours water or other aqueous fluid into the fill tube 15 until water drips out the steam outlet 25. This indicates the appliance is full. The plug 17 is reinserted, the sauna is turned upright, the desired attachment is attached to the outlet end, the sliding ring 23 is adjusted and the power cord 46 is plugged in. After a wait of about three minutes for heat up of the water, steam emerges from the steam outlet 25 and the appliance is ready to use.

We claim:

1. A vapor generating device comprising:
   a housing including a base portion and an upper portion extending from said base portion, said base portion having an upright use position and an inverted filling position, said base portion having an inlet suitable for receiving liquid therethrough when in said inverted filling position, said upper portion having an outlet portion;
   container means within said housing communicating with said inlet for containing liquid received therein through said inlet;
   electrically energized vaporizing means at least partly disposed in said container means for vaporizing the liquid; and
   at least one passageway interconnecting said container means to said outlet portion for conveying the liquid and vapor to said outlet, said container means and at least one passageway being so configured and arranged that said liquid outlets through at least part of said outlet portion upon the filling of said container means beyond a certain volume when said base portion is in said inverted position, said at least one passageway being oriented relative to said container means so as to retain at most said certain volume within said container means when said housing is in any position subsequent to said filling.

2. The vapor generating device of claim 1 further including energizing means for providing electrically to energize said vaporizing means.

3. The vapor generating device of claim 1 further comprising means associated with said housing for supplying air to said generated vapor for mixing therewith.

4. The vapor generating device of claim 3 wherein said air supplying means includes air inlets extending through said housing, said air inlets being interconnected with said at least one passageway.

5. The vapor generating device of claim 4 wherein said air supplying means includes control means for controlling the supply of air through said air inlets.

6. The vapor generating device of claim 5 wherein said control means includes a slidable ring circumferentially surrounding said housing, said air inlets having openings in said housing adjustably coverable by said slidable ring.

7. The vapor generating device of claim 1 further comprising air mixing means within said housing for mixing air with said vapor and conveying said mixture through said outlet portion.

8. The vapor generating device of claim 7 wherein said air mixing means includes a fan and air channels extending through said outlet portion to said fan.

9. The vapor generating device of claim 8 further including a hollow attachment to said outlet portion for conveying of the steam-air mixture therethrough.

10. The vapor generating device of claim 9 wherein said attachment includes a portion for controlling air passage through said air channels.

11. The vapor generating device of claim 9 wherein said attachment is adapted for facial use.

12. The vapor generating device of claim 9 wherein said attachment is a tube for concentrating said steam-air mixture.

13. The vapor generating device of claim 9 wherein said attachment includes a brush portion.

14. The vapor generating device of claim 9 wherein said attachment includes a sponge portion.

15. The vapor generating device of claim 1 wherein said inlet extends through the bottom of said base portion.

16. The vapor generating device of claim 1 wherein said container means includes an annular tank, a chamber interconnected to and centrally extended through said annular tank, said at least one passageway being interconnected with said central chamber and angularly disposed relative thereto.

17. The vapor generating device of claim 16 wherein said annular tank includes an upper portion and lower portion interconnected through a constricted passageway, said lower portion being interconnected to said central chamber.

18. The vapor generating device of claim 17 wherein said annular tank and central chamber cooperate so as to have a suitable volume and configuration for retention of said certain fluid volume therein and for precluding loss of any of said certain volume through said angularly disposed at least one passageway when said housing is in any position subsequent to said filling.

19. The vapor generating device of claim 1 wherein said vaporizing means includes an electrically energized heater.

20. The vapor generating device of claim 1 wherein said vapor is applied facially.

* * * * *